(12) United States Patent
Kitamura et al.

(10) Patent No.: US 11,298,301 B2
(45) Date of Patent: Apr. 12, 2022

(54) OIL-IN-WATER EMULSIFIED COSMETIC

(71) Applicant: LVMH RECHERCHE, Saint Jean de Braye (FR)

(72) Inventors: Miyako Kitamura, Tokyo (JP); Mai Ozawa, Tokyo (JP); Takayoshi Sakoda, Tokyo (JP)

(73) Assignee: LVMH RECHERCHE, Saint Jean de Braye (FR)

( * ) Notice: Subject to any disclaimer, the term of this patent is extended or adjusted under 35 U.S.C. 154(b) by 266 days.

(21) Appl. No.: 16/612,626

(22) PCT Filed: Dec. 22, 2017

(86) PCT No.: PCT/EP2017/084551
§ 371 (c)(1),
(2) Date: Nov. 11, 2019

(87) PCT Pub. No.: WO2019/120590
PCT Pub. Date: Jun. 27, 2019

(65) Prior Publication Data
US 2020/0197264 A1    Jun. 25, 2020

(51) Int. Cl.
*A61K 8/06* (2006.01)
*A61K 8/42* (2006.01)
*A61K 8/92* (2006.01)
*A61Q 19/00* (2006.01)

(52) U.S. Cl.
CPC ............... *A61K 8/062* (2013.01); *A61K 8/42* (2013.01); *A61K 8/92* (2013.01); *A61Q 19/007* (2013.01)

(58) Field of Classification Search
CPC .......... A61K 8/06; A61K 8/062; A61K 8/375; A61K 8/39; A61K 8/8158; A61K 8/86; A61Q 19/00
See application file for complete search history.

(56) References Cited

U.S. PATENT DOCUMENTS

2009/0022680 A1* 1/2009 L'Alloret ............... A61K 8/06
                                                          424/70.11

FOREIGN PATENT DOCUMENTS

| EP | 3173064 | 5/2017 | |
| EP | 3213743 | 9/2017 | |
| JP | 2002087931 | 3/2002 | |
| JP | 2016088868 | 5/2016 | |
| JP | 3173064 A1 * | 5/2017 | ............ A61K 8/891 |
| JP | 2017081868 | 5/2017 | |
| JP | 2017105766 | 6/2017 | |

OTHER PUBLICATIONS

International Search Report and Written Opinion issued for International Patent Application No. PCT/EP2017/084551, dated Aug. 17, 2018, 8 pages.

* cited by examiner

*Primary Examiner* — Audrea B Coniglio
(74) *Attorney, Agent, or Firm* — Hamre, Schumann, Mueller & Larson, P.C.

(57) ABSTRACT

An oil-in-water emulsified cosmetic comprising an aqueous medium, an anionic surfactant, an oil agent, an amphiphilic polymer selected from the group consisting of hydrophobic group-modified hydrophilic urethane polymers, (meth) acrylic polymers having a side chain including hydrophilic and hydrophobic groups, and hydrophobic group-modified hydrophilic polysaccharides, and a charge neutralizer, wherein the cosmetic has a viscosity of 10,000 mPa·s or higher at 25° C.

9 Claims, No Drawings

OIL-IN-WATER EMULSIFIED COSMETIC

TECHNICAL FIELD

The present invention relates to an oil-in-water emulsified cosmetic.

BACKGROUND ART

Oil-in-water emulsions, one of the types of formulations used in cosmetics, exhibit high nourishing and protective effects due to appropriate quantities of oil agents in the formulations, and such formulations with especially high viscosity are often used in common skin care formulations such as cosmetic creams or essence.

Finely dispersed emulsions are oil-in-water emulsified cosmetics that have been emulsified at a high pressure, and it is believed that such emulsions are generally able to stably accommodate large amounts of oils (PTL 1). In addition, it has been reported that high-pressure emulsification of specific components can yield a gel-like oil-in-water emulsified composition with satisfactory transparency and long-term stability (PTL 2).

CITATION LIST

Patent Literature

[PTL 1] Japanese Unexamined Patent Application Publication No. 2002-87931
[PTL 2] Japanese Unexamined Patent Application Publication No. 2017-105766

SUMMARY OF INVENTION

Technical Problem

The oil-in-water emulsified cosmetic described in PTL 1 is poorly suited for practical use because its stability cannot be maintained depending on the additives that are included, while the gel-like oil-in-water emulsified composition of PTL 2 tends to be sticky and exhibit a feel that is undesirable for a cosmetic.

It is an object of the invention to provide an oil-in-water emulsified cosmetic that can accommodate large amounts of oil agent while exhibiting excellent stability without stickiness.

Solution to Problem

The present invention provides an oil-in-water emulsified cosmetic comprising (A) an aqueous medium, (B) an anionic surfactant, (C) an oil agent, (D) an amphiphilic polymer, selected from the group consisting of hydrophobic group-modified hydrophilic urethane polymers, (meth) acrylic polymers having a side chain including hydrophilic and hydrophobic groups, and hydrophobic group-modified hydrophilic polysaccharides, and (E) a charge neutralizer, the cosmetic having the feature of a viscosity of 10,000 mPa·s or higher at 25° C. The "aqueous medium (A)" will hereunder also be referred to simply as "component (A)", and the other components will be referred to similarly. The term "(meth)acryl" refers to acryl or methacryl, and the same applies to analogous skeltons.

The oil-in-water emulsified cosmetic of the invention can accommodate large amounts of oil while exhibiting excellent stability without stickiness, despite the large oil content. Moreover, it has an excellent nourishing effect and an excellent texture, including a watery light sensation, and a feeling of penetrating into the skin. In addition to these properties it also exhibits the features of satisfactory light resistance and low discoloration/fading.

Common oil-in-water emulsified cosmetics have low penetration through skin and tend to produce a heavy, sticky feel. The present inventors have found that the reason this occurs is because achieving stable emulsification and dispersion of oil in a formulation in a suitable amount to exhibit an adequate nourishing effect requires addition of excessive amounts of surfactant and co-surfactant, waxes or thickeners, and it is these components that produce the heavy feel and stickiness. Consequently, cosmetic formulations that are stickiness free and have a watery sensation, while also providing a high nourishing effect by high penetration, have not existed.

While it is possible to obtain oil-in-water emulsions that exhibit a gel-like appearance by implementing the methods for obtaining fine emulsions disclosed in the aforementioned patent documents, this is believed to be possible because particles with uniform sizes and electrostatic repulsion between them are situated in close range on the surface, and their mutual electrostatic repulsion causes formation of a regular crystal-like structure. With such emulsions it is possible to add large amounts of oils that have nourishing effects, without including elements that would produce heaviness and stickiness, but such gels comprising fine emulsions tend to become unstable with time, gradually losing their viscosity and potentially leading to coalescence when various commonly used additives, such as charge neutralizers, have been added to the cosmetic.

Considering the principle by which gels composed of fine emulsions form, it is thought that the reason for this phenomenon is that effects from the internal or external environment cause progressive weakness of the electrostatic repulsion between emulsion particles that is responsible for the crystal-like structure, and that this results in coalescence.

PTLs 1 and 2 do not deal with a solution to this problem, and in the case of PTL 1, the stability is sometimes inadequate when various commonly used additives have been added to the cosmetic. In the case of PTL 2, stickiness possibly occurs. The stickiness is presumably caused by the need for addition of large amounts of surfactant to stabilize the cosmetic.

In contrast to these cosmetics, the oil-in-water emulsified cosmetic of the invention is a cosmetic that has a non-sticky, light feel, exhibits a high nourishing effect due to high penetration, and has excellent stability over time. While these effects are provided by the compounds of components (A) to (E), it is component (D) in particular that increases the viscosity of the formulation by interaction between the emulsion particles with its own hydrophobic groups, effectively contributes to gel formation, and dramatically maintains viscosity over time, in the case where the viscosity immediately after formulation and after standing for one month at 50° C. are compared, for example.

When a water-soluble polymer other than component (D) is used, examples being xanthan gum, or an anionic polymer such as a Carbomer or an alkyl copolymer, or a nonionic polymer such as hydroxyethyl cellulose, electrostatic repulsion between the emulsion particles is inhibited, and as a result, the viscosity is lowered and a stable gel-like oil-in-water emulsified cosmetic cannot be obtained.

Since a gel composed of a fine emulsion maintains the stability of the particles by electrostatic repulsion, it is imagined that the stability is compromised when an electrolyte such as component (E) is added. According to the invention, however, cooperative interaction by the other components, and especially component (D), results in excellent stability over time without losing stability of particles. In addition, the texture including the nourishing effect, watery light sensation and the feeling of penetration into the skin, is also improved.

The amphiphilic polymer can be a hydrophilic polymer having hydrophobic groups in side chains and/or end chains. For example, the amphiphilic polymer may be a hydrophobic group-modified hydrophilic urethane polymer and/or a hydrophobic group-modified hydrophilic polysaccharide, in which case, preferably, the hydrophobic group-modified hydrophilic urethane polymer contains hydrophobic group-modified polyether urethane including polyoxyalkylene component, and the hydrophobic group-modified hydrophilic polysaccharide contains a hydrophobic group-modified hydroxyalkyl alkylcellulose. Using such an amphiphilic polymer especially exhibits nourishing effect, watery light sensation, non-stickiness, penetration into the skin, and adequate spreading, and the features of satisfactory light resistance and low discoloration are notably achieved.

The oil-in-water emulsified cosmetic of the invention may have an oil agent content ratio of 20 mass % or greater based on the total mass of the oil-in-water emulsified cosmetic. The nourishing effect will be notably increased by adding the oil in such a large amount.

As the oil agent, furthermore, the oil-in-water emulsified cosmetic of the invention can contain a liquid oil. The liquid oil is preferably a non-polar liquid oil, a silicone liquid oil or a mixture thereof. Using such an oil agent increases emulsified cosmetic stability.

The oil-in-water emulsified cosmetic of the invention is obtainable by emulsification at a pressure of 100 MPa or higher. Even if the oil content is high, emulsification at such a pressure level can easily yield an oil-in-water emulsified cosmetic having a very excellent texture such as excellent emulsified stability, reduced stickiness, as well as a nourishing effect, watery light sensation and the feeling of penetration into the skin. It is to be noted that with oil-in-water emulsified cosmetics prepared by common dispersion steps, separation usually takes place immediately after their formulation.

Advantageous Effects of Invention

The invention can provide an oil-in-water emulsified cosmetic that is able to accommodate large amounts of oil while exhibiting excellent stability without stickiness.

DESCRIPTION OF EMBODIMENTS

Component (A) in the oil-in-water emulsified cosmetic of this embodiment is an aqueous medium which contains at least water, as the medium for components (B) to (E). Component (A) may consist of water alone or it may comprise water-soluble components other than components (B), (D) and (E).

Water-soluble components include polyols, monools, polysaccharides, nonionic surfactants, amphoteric surfactants, preservatives, synthetic water-soluble polymers, ultraviolet absorbers, ultraviolet scatterings and the like. Water-soluble components also include antimicrobial agents, anti-inflammatory agents, vitamins and amino acids.

Examples of polyols include butylene glycol, pentylene glycol and glycerin. Polysaccharides include galactomannans such as locust bean gum, guar gum and fenugreek gum; plant polysaccharides such as carrageenan, galactan, gum arabic, pectin, mannan and starch; and microorganic polysaccharides such as xanthan gum, dextran, succinoglucan, curdlan and gellan gum.

As nonionic surfactants there may be used ethylene oxide addition products of sorbitan fatty acid esters such as polysorbate 20, polysorbate 60, polysorbate 65 and polysorbate 80; and ethylene oxide addition products of alkyl ethers such as Oleth-2, Ceteth-6 and Laureth-4. Hydrogenated lecithin is an example of an amphoteric surfactant.

Phenoxyethanol is an example of an preservatives, and ethanol is an example of a monool.

Component (B) in the oil-in-water emulsified cosmetic of this embodiment is an anionic surfactant.

Anionic surfactants include fatty acid soaps such as lauric acid salts and palmitic acid salts; phosphoric acid ester salts such as cetylphosphoric acid salts; N-acylglutamic acid salts such as N-lauroylglutamic acid salts and N-myristoyl-L-glutamic acid salts; N-acylglutamic acid salts such as N-lauroylglutamic acid salts, N-myristoylglutamic acid salts and N-stearoylglutamic acid salts; N-acylglycine salts such as N-lauroylglycine salts, N-myristoylglycine salts and N-stearoylglycine salts; N-acylalanine salts such as N-lauroylalanine salts, N-myristoylalanine salts and N-stearoylalanine salts; N-acylaspartic acid salts such as N-lauroylaspartic acid salts, N-myristoylaspartic acid salts and N-stearoylaspartic acid salts; long-chain acyl lower alkyl taurine salts such as N-cocoyl-N-methyltaurine salts, N-lauroyl-N-methyltaurine salts, N-myristoyl-N-methyltaurine salts, N-stearoyl-N-methyltaurine salts and N-cocoyltaurine salts; and sodium lysine dilauroylglutamate, sodium surfactin and the like. Particularly useful among these are N-acylglutamic acid salts such as sodium N-stearoylglutamate.

Component (C) in the oil-in-water emulsified cosmetic of this embodiment is an oil agent. The oil agent added is preferably a liquid oil. The oil agent includes a polar oil, a non-polar oil and a silicone oil.

Oil agents include isononyl isononanoate, isotridecyl isononanoate, ethylhexyl palmitate, cetyl ethylhexanoate, neopentylglycol diethylhexanoate, neopentylglycol dicaprate, triethylhexanoin, glyceryl tri(caprylate/caprate), triisostearin, trimethylolpropane triisostearate, pentaerythrityl tetraethylhexanoate, pentaerythrityl tetraisostearate, polyglyceryl-2 tetraisostearate, propanediol di(caprylate/caprate), propanediol diisostearate and polyglyceryl-6 octacaprylate.

Furthermore, oil agents include octyldodecyl lactate, diisostearyl malate, polyglyceryl-2 isostearate, polyglyceryl-2 diisostearate, polyglyceryl-2 triisostearate, ditrimethylolpropane (isostearate/sebacate) oligoester, erythrityl triethylhexanoate, dipentaerythrityl tripolyhydroxystearate, isostearic acid trehalose esters, dipentaerythrityl pentaisostearate, ethylhexyl hydroxystearate, polyhydroxystearic acid, liquid paraffin, squalane, α-olefin oligomer, vaseline, polyisobutylene, polybutene, isododecane, isohexadecane and heavy liquid isoparaffin.

Silicone oils may also be used as oil agents. Examples of silicone oils include dimethylpolysiloxane, methylphenylpolysiloxane, decamethylcyclopentasiloxane, octamethylcyclotetrasiloxane, trimethylsiloxysilicic acid and high-polymerized methylphenylpolysiloxane.

From among these oil agents, it is preferred to add one or more liquid non-polar oils or liquid silicone oils. Suitable liquid non-polar oils include squalane, isododecane and α-olefin oligomers, and suitable liquid silicone oils include dimethylpolysiloxane and decamethylcyclopentasiloxane.

Other oil agents that may be used in addition to these include paste oils such as cholesteryl hydroxystearate, phytostearyl hydroxystearate, phytostearyl oleate, dipentaerythrityl hexa(hydroxystearate/stearate/rosinate), dipentaerythrityl tetra(hydroxystearate/isostearate), dipentaerythrityl hexahydroxystearate, glyceryl (ethylhexanoate/stearate/adipate), glyceryl tri(caprylate/caprate/myristate/stearate), hydrogenated palm oil, vaseline, dipentaerythrityl hexa(behenate/benzoate/ethylhexanoate), plant oil pastes (vegetable oils), shea butter (*Butyrospermum parkii*), mango seed butter (*Mangifera indica*) and avocado butter (*Persea gratissima*). The amount of paste oils and the amount of waxes in the emulsified cosmetic are preferably limited in order not to impart stickiness to the product. According to one embodiment of the invention, the emulsified cosmetic contains less than 1% waxes, and preferably contains no wax.

Component (D) in the oil-in-water emulsified cosmetic of this embodiment is an amphiphilic polymer, and is selected from the group consisting of hydrophobic group-modified hydrophilic urethane polymers, (meth)acrylic polymers having a side chain including hydrophilic and hydrophobic groups, and hydrophobic group-modified hydrophilic polysaccharides.

In the amphiphilic polymer, hydrophobic group is a group having hydrophobic properties, and hydrophobic group modification is the addition of a hydrophobic group to the molecule.

The hydrophobic groups may be C1-30 hydrocarbon groups, which are typically C1-30 straight-chain or branched alkyl groups. The number of carbon atoms is preferably 6 to 30 and more preferably 12 to 24.

The straight-chain or branched alkyl groups may be dodecyl (lauryl), tridecyl, tetradecyl, pentadecyl, hexadecyl, heptadecyl, octadecyl, nonadecyl, eicosyl, docosyl (behenyl) or decyltetradecyl groups.

(Hydrophobic group-modified) hydrophilic urethane polymers include (hydrophobic group-modified) polyether urethane, said polyether urethane including polyalkylene oxide component, such as polyethylene oxide and polypropylene oxide. Such useful urethane polymers include ones having the aforementioned hydrophobic groups introduced at the ends or side chains of a hydrophilic urethane polymer having PEO blocks, PEO/PPO blocks, PEO/PPO/PEO blocks or PPO/PEO/PPO blocks. PEO stands for polyethylene oxide and PPO for polypropylene oxide, and these are sometimes listed as PEG (polyethylene glycol) and PPG (polypropylene glycol) respectively. The isocyanate forming a urethane may be an aromatic isocyanate, aliphatic isocyanate or alicyclic isocyanate.

Hydrophobic group-modified hydrophilic urethane polymers include (PEG-240/decyltetradeceth-20/HDI) copolymer (trade name; ADEKA. NOL™ GT-700) and PPG-12/methylenediphenyl diisocyanate copolymer (trade name: EXPERTGEL™ EG412).

Useful (meth)acrylic polymers having a side chain including hydrophilic and hydrophobic groups are those of a (meth)acrylic polymer with a hydrophilic group such as a carboxy group, which has a side chain including hydrophilic and hydrophobic groups.

Such polymers include (meth)acrylic polymers having a carboxy group, and an amphiphilic side chain that are composed of a hydrophobic block and a hydrophilic block and are bonded to the main chain from the hydrophilic block side.

A hydrophobic block is one that has a length of more than one carbon atom and is itself hydrophobic, and typically it is a hydrocarbon skelton. The hydrophobic block is preferably a hydrocarbon skelton of 12 to 24 carbon atoms.

A hydrophilic block is one that has a length of more than one carbon atom and is itself hydrophilic, and typically it is a polyoxyalkylene skelton. The hydrophilic block is preferably composed of a polyoxyethylene skelton, which may have 10 to 30 oxyethylene repeats. That is, it preferably has a —(CH$_2$CH$_2$O)$_n$— skelton where n is 10 to 30, the value of n being preferably 12 to 25 and more preferably 20 to 25. The hydrophilic block may be directly bonded to the main chain, or bonded via a linker. The linker may be an oxycarbonyl group (—CO—O—), the —O— portion preferably being bonded to a carbon atom of the polyoxyalkylene skelton.

The (meth)acrylic polymer may have an alkoxycarbonyl group, the alkyl group of the alkoxycarbonyl group preferably being a C1-24 alkyl group.

Particularly preferred are polymers comprising (meth)acrylic acid, alkyl (meth)acrylate esters and polyoxyethylene monoalkyl (meth)acrylate ether esters as repeating units [(meth)acrylic acid/alkyl (meth)acrylate/(meth)acrylic acid-POE-monoalkyl ether ester copolymers]. Examples of such components include Aculyn™22 and Aculyn™28, by Dow Chemical Corp.

A useful (meth)acrylic polymer having a side chain including hydrophilic and hydrophobic groups is (meth)acrylic polymer having an amphiphilic side chain composed of a hydrophobic block and a hydrophilic block and being bonded to the main chain at the hydrophilic block side, and a substituted or an unsubstituted amide group. Further, the amphiphilic side chain has hydrophilic and hydrophobic blocks, and is thus equivalent to side chain including hydrophilic and hydrophobic groups. The hydrophobic block and hydrophilic block are the same as described above, and the hydrogen atoms of the amide group may be substituted with an alkyl-modified aminoalkylsulfonic acid group such as an alkyl-modified taurine group. Such components include acryloyldimethyltaurine ammonium Beheneth-25 methacrylate crosspolymer (trade name: ARISTOFLEX™ HMB).

Other useful (meth)acrylic polymers having a side chain including hydrophilic and hydrophobic groups include (meth)acrylic polymers comprising N-vinylpyrrolidone, and (meth)acrylamide modified with a substituted group including hydrophilic and hydrophobic groups, as monomer units. The substituted group include alkyl-modified aminoalkylsulfonic acid groups such as alkyl-modified taurine groups. An example of an alkyl-modified taurine group may include a dimethyl taurine group (—NH—C(CH$_3$)$_2$—CH$_2$—SO$_3$H). The alkyl-modified taurine group constitutes the side chains, with —SO$_3$H (or a salt thereof) being a hydrophilic group and the portion between —NH and —SO$_3$H (or a salt thereof) being a hydrophobic group. One such component is (acryloyldimethyltaurine ammonium/VP) copolymer (trade name: ARISTOFLEX™ AVC).

Other useful hydrophilic (meth)acrylic polymers having a side chain including hydrophilic and hydrophobic groups include (meth)acrylic polymers comprising (meth)acrylic acid and hydroxyalkyl (meth)acrylate as monomer units. In such cases, the hydroxyalkyl group constitutes the side chain, with the hydroxy group in the hydroxyalkyl group being a hydrophilic group and the alkyl group being a hydrophobic group. The number of carbon atoms of the alkyl group of the hydroxyalkyl portion may be 3 to 12. One such component is acrylate copolymer (trade name: BALANCE™ RCF™g).

Useful hydrophobic group-modified hydrophilic polysaccharides include hydroxyalkyl alkylcelluloses (such as hydroxypropyl methyl cellulose) that are modified with the aforementioned hydrophobic groups. One such component is hydrophobized hydroxypropyl methyl cellulose, wherein the hydrophobic group is a stearoyl group (trade name: SANGELOSE™ 90L).

Component (E) in the oil-in-water emulsified cosmetic of this embodiment is a charge neutralizer. A charge neutralizer can be selected from buffers typical ones including citric acid, sodium phosphate, disodium phosphate and sodium hydrogensulfite. Other buffers, antioxidants, pH regulators, chelating agents, whitening agents, plant extracts, antimicrobial agents, anti-inflammatory agents, vitamins, amino acids and the like, which are ionized in water, may also be used as charge neutralizers. A charge neutralizer can also be called an electrolyte by one skilled in the art.

The viscosity of the oil-in-water emulsified cosmetic at 25° C. is preferably 10,000 mPa·s or greater. The viscosity at 25° C. is more preferably 50,000 to 300,000 mPa·s, and preferably a gel-like appearance is exhibited.

The oil-in-water emulsified cosmetic is obtainable by emulsification at a pressure of 100 MPa or higher, the pressure preferably being 150 MPa or higher and more preferably 200 MPa or higher, and preferably being no higher than 500 MPa.

The emulsification can be carried out using a high-pressure homogenizer. The high-pressure homogenizer is an apparatus that carries out emulsification by pressurizing a fluid with a pump and ejecting it through fine slits provided in the flow channel.

The oil-in-water emulsified cosmetic can be obtained by mixing components (A) to (E) and using a high-pressure homogenizer for emulsification at a pressure of 200 MPa, for example.

Therefore, the present invention also relates to a process for preparing the oil-in-water emulsified cosmetic as described above. The process comprises a step of emulsifying a mixture of components (A) to (E) in a high-pressure homogenizer at a pressure of 100 MPa or higher, the pressure preferably being 150 MPa or higher and more preferably 200 MPa or higher, and preferably being no higher than 500 MPa. The pressure can be 200 MPa.

In a first step of the process for preparing, the aqueous medium (A), the anionic surfactant (B) and polymer (C) can be heated at a temperature T, mixed and stirred (for example at a speed of 2500 rpm) using a stirrer, in order to obtain a first mixture.

In a second step, the oil agent (D) and charge neutralizer (E) can be added in that order to the first mixture that has been obtained in the first step, to obtain a second mixture that can be stirred under the same conditions as in the first step. Mixing and adding the components in the second step is preferably performed at a temperature that is equal to temperature T.

In a third step, the second mixture is cooled from temperature T to room temperature, and then emulsified in a high-pressure homogenizer (for example model Star Burst: product of Sugino Machine, Ltd) to obtain the oil-in-water emulsified cosmetic. The pressure is preferably a pressure being 100 MPa or higher, preferably being 150 MPa or higher and more preferably 200 MPa or higher, and preferably being no higher than 500 MPa. The pressure can be 200 MPa.

The content ratio of component (C) in the oil-in-water emulsified cosmetic is preferably 20 mass % or greater, and more preferably 20 to 60 mass %. Preferably, the content ratio of component (B) is 0.1 to 10 mass %, the content ratio of component (D) is 0.01 to 2 mass % and the content ratio of component (E) is 0.001 to 5 mass %. Component (A) will constitute the remaining content. The lower limit for the content ratio of component (C) is preferably 30 mass %, more preferably 40 mass %, and the lower limit may be 50 mass %. Component (C) preferably comprises (C1) at least one selected from the group consisting of a non-polar oil and a silicone oil, and (C2) oil other than this, and the content ratio of the C1 component with respect to the entire oil agent is preferably 50 to 98 mass %. More preferably 60 to 98 mass %, and even more preferably 70 to 95 mass %. These contents are based on the total mass of the oil-in-water emulsified cosmetic.

The oil-in-water emulsified cosmetic exhibits the properties of a high nourishing effect, a watery light sensation, stickiness free and excellent stability. The high nourishing effect is attributed to the appropriate amount of oil encapsulated in the fine emulsion, and the watery light sensation is attributed to a crystalline-like structure formed by electrostatic repulsion between the emulsion particles composed of an anionic surfactant. The stickiness free is due to the low content of water-soluble polymers, surfactants and co-surfactants, and the stability is attributed to retention of the crystalline-like structure arising from component (D).

The invention also relates to a method of skin care comprising a step of applying on skin an oil-in-water emulsified cosmetic as described above. Skin care comprises skin nourishing, which can be advantageously obtained together with a watery light sensation, a stickiness free sensation and/or a feeling of penetrating into skin. In a particular embodiment, the invention relates to a method of nourishing skin comprising a step of applying to the skin an oil-in-water emulsified cosmetic as described above.

The invention will now be illustrated by examples, with the understanding that the invention is not meant to be limited to these examples.

Examples 1 to 9 and Comparative Examples 1 to 5

Oil-in-water emulsified cosmetics with different types of constituent polymers and contents as listed in Table 1 were prepared by the following method (Examples 1 to 9 and Comparative Examples 1 to 5). First, the aqueous medium (column "a"), the anionic surfactant (column "b") and polymer (column "c") were heated, and then mixed and stirred at 2500 rpm using a stirrer. The oil agent (column "d") and charge neutralizer (column "e") were then added in that order, and the components were stirred under the same conditions to obtain a mixture. After cooling the mixture to room temperature, a high-pressure homogenizer (Star Burst: product of Sugino Machine, Ltd.) was used for treatment at a pressure of 200 MPa to obtain an oil-in-water emulsified cosmetic. The contents (mass %) of each of the materials were as shown in Table 1.

Organoleptic Evaluation

The oil-in-water emulsified cosmetics of Examples 1 to 9 and Comparative Examples 1 to 5 were evaluated for nourishing effect, watery light sensation, stickiness free and feeling of penetration into the skin, in a single-use test on skin by an expert cosmetic evaluation panel from an organization to which the present inventors belong, the evaluation being made on the following scale. The results are shown in Table 1.

(1) Nourishing effect, watery light sensation, and feeling of penetration into skin
A: Strong
B: Moderate
C: Almost none
D: None
(2) Stickiness free
A: Absolutely no stickiness
B: Almost no stickiness
C: Slight stickiness
D: Stickiness Outer Appearance Evaluation The oil-in-water emulsified cosmetics of Examples 1 to 9 and Comparative Examples 1 to 5 were evaluated for the presence of any discoloration. Each of the prepared oil-in-water emulsified cosmetics was filled into a transparent container and sealed with a cap, and the presence of any discoloration in each oil-in-water emulsified cosmetic was evaluated after storage for one month under natural lighting. Evaluation was made on a 4-level scale from A to D in order of lower discoloration, where samples with absolutely no discoloration were defined as "A". The results are shown in Table 1.

Evaluation of Stability

The oil-in-water emulsified cosmetics of Examples 1 to 9 and Comparative Examples 1 to 5 were evaluated for their stability over time. Each cosmetic was filled into a transparent container and sealed with a cap, and then stored for 1 month at 50° C. Any separation between the oil phase and aqueous phase after storage was observed. On the day following formulation and after one month of storage at 50° C., the shear viscosity of each cosmetic was measured at 25° C. using a rotating viscometer (Rheolab QC by Anton Paar GmbH) (rotational speed: 10 rpm). The degree of oil phase-aqueous phase separation and the change in viscosity from the day following formulation until one month of storage at 50° C. were observed, and evaluation was made on a 4-level scale of A to D in order of less change from the initial condition. The results are shown in Table 1.

TABLE 1

| | | Ex. 1 | Ex. 2 | Ex. 3 | Ex. 4 | Ex. 5 | Ex. 6 | Ex. 7 | Ex. 8 |
|---|---|---|---|---|---|---|---|---|---|
| A (Aqueous medium) | Butylene glycol | 5 | 5 | 5 | 5 | 5 | 5 | 5 | 5 |
| | Pentylene glycol | 2 | 2 | 2 | 2 | 2 | 2 | 2 | 2 |
| | Glycerin | 5 | 5 | 5 | 5 | 5 | 5 | 5 | 5 |
| | Phenoxyethanol | 0.5 | 0.5 | 0.5 | 0.5 | 0.5 | 0.5 | 0.5 | 0.5 |
| | Water | rem | rem | rem | rem | rem | rem | rem | rem |
| B (Anionic Surfactant) | Sodium stearoylglutamate (AMISOFT HS-11 PF) | 1.5 | 1.5 | 1.5 | 1.5 | 1.5 | 1.5 | 1.5 | 1.5 |
| C (Liquid Oil agent) | Dimethylpolysiloxane | 10 | 10 | 10 | 10 | 10 | 10 | 10 | 10 |
| | Decamethylcyclopentasiloxane | 10 | 10 | 10 | 10 | 10 | 10 | 10 | 10 |
| | Squalane | 5 | 5 | 5 | 5 | 5 | 5 | 5 | 5 |
| | Isododecane | 10 | 10 | 10 | 10 | 10 | 10 | 10 | 10 |
| | Polyglyceryl-2 triisostearate | 5 | 5 | 5 | 5 | 5 | 5 | 5 | 5 |
| | Perfume | 0.1 | 0.1 | 0.1 | 0.1 | 0.1 | 0.1 | 0.1 | 0.1 |
| D (Polymer) | (PEG-240/decyltetradeceth-20/HDI) copolymer (ADEKANOL GT-700) | 0.1 | 0.2 | 0.3 | — | — | — | — | — |
| | (PPG-12/methylenediphenyl diisocyanate) copolymer (EXPERTGEL EG412) | — | — | — | 0.1 | — | — | — | — |
| | Hydrophobized hydroxyl propyl methyl cellulose (SANGELOSE 90 L) | — | — | — | — | 0.1 | — | — | — |
| | (Acryloyldimethyltaurine ammonium/VP)copolymer (ARISTOFLEX AVC) | — | — | — | — | — | 0.1 | — | — |
| | (Acryloyldimethyltaurine ammonium/Beheneth-25 methacrylate) crosspolymer (ARISTOFLEX HMB) | — | — | — | — | — | — | 0.1 | — |
| | Acrylate/Beheneth-25 methacrylate copolymer (ACULYN 28) | — | — | — | — | — | — | — | 0.5 |
| | Acrylate copolymer (BALANCE RCFg) | — | — | — | — | — | — | — | — |
| | Xanthan gum | — | — | — | — | — | — | — | — |
| | Carboxyvinyl polymer | — | — | — | — | — | — | — | — |
| | (Acrylates/alkyl acrylate (C10-30)) crosspolymer | — | — | — | — | — | — | — | — |
| | Hydroxyethyl cellulose | — | — | — | — | — | — | — | — |
| E (Charge neutralizer) | Citric acid | 0.01 | 0.01 | 0.01 | 0.01 | 0.01 | 0.01 | 0.01 | 0.01 |
| | Total amount (mass %) | 100 | 100 | 100 | 100 | 100 | 100 | 100 | 100 |

TABLE 1-continued

|  |  | | | | | | | | |
|---|---|---|---|---|---|---|---|---|---|
| Organo evaluation | Nourishing effect | A | A | A | A | A | A | A | A |
|  | Watery light sensation | A | A | B | A | A | B | B | B |
|  | Stickiness free | A | A | B | A | A | B | B | B |
|  | Feeling of penetration into skin | A | A | A | A | A | A | A | A |
| Outer appearance | Presence of any discoloration | A | A | A | A | A | A | A | A |
|  | Stability evaluation | A | A | A | A | A | B | B | B |

|  |  | Ex. 9 | Comparative 1 | Comparative 2 | Comparative 3 | Comparative 4 | Comparative 5 |
|---|---|---|---|---|---|---|---|
| A (Aqueous medium) | Butylene glycol | 5 | 5 | 5 | 5 | 5 | 5 |
|  | Pentylene glycol | 2 | 2 | 2 | 2 | 2 | 2 |
|  | Glycerin | 5 | 5 | 5 | 5 | 5 | 5 |
|  | Phenoxyethanol | 0.5 | 0.5 | 0.5 | 0.5 | 0.5 | 0.5 |
|  | Water | rem | rem | rem | rem | rem | rem |
| B (Anionic Surfactant) | Sodium stearoylglutamate (AMISOFT HS-11 PF) | 1.5 | 1.5 | 1.5 | 1.5 | 1.5 | 1.5 |
| C (Liquid Oil agent) | Dimethylpolysiloxane | 10 | 10 | 10 | 10 | 10 | 10 |
|  | Decamethylcyclopentasiloxane | 10 | 10 | 10 | 10 | 10 | 10 |
|  | Squalane | 5 | 5 | 5 | 5 | 5 | 5 |
|  | Isododecane | 10 | 10 | 10 | 10 | 10 | 10 |
|  | Polyglyceryl-2 triisostearate | 5 | 5 | 5 | 5 | 5 | 5 |
|  | Perfume | 0.1 | 0.1 | 0.1 | 0.1 | 0.1 | 0.1 |
| D (Polymer) | (PEG-240/decyltetradeceth-20/HDI) copolymer (ADEKANOL GT-700) | — | — | — | — | — | — |
|  | (PPG-12/methylenediphenyl diisocyanate) copolymer (EXPERTGEL EG412) | — | — | — | — | — | — |
|  | Hydrophobized hydroxyl propyl methyl cellulose (SANGELOSE 90 L) | — | — | — | — | — | — |
|  | (Acryloyldimethyltaurine ammonium/VP)copolymer (ARISTOFLEX AVC) | — | — | — | — | — | — |
|  | (Acryloyldimethyltaurine ammonium/Beheneth-25 methacrylate) crosspolymer (ARISTOFLEX HMB) | — | — | — | — | — | — |
|  | Acrylate/Beheneth-25 methacrylate copolymer (ACULYN 28) | — | — | — | — | — | — |
|  | Acrylate copolymer (BALANCE RCFg) | 0.33 | — | — | — | — | — |
|  | Xanthan gum | — | — | 0.1 | — | — | — |
|  | Carboxyvinyl polymer | — | — | — | 0.1 | — | — |
|  | (Acrylates/alkyl acrylate (C10-30)) crosspolymer | — | — | — | — | 0.1 | — |
|  | Hydroxyethyl cellulose | — | — | — | — | — | 0.1 |
| E (Charge neutralizer) | Citric acid | 0.01 | 0.01 | 0.01 | 0.01 | 0.01 | 0.01 |
|  | Total amount (mass %) | 100 | 100 | 100 | 100 | 100 | 100 |
| Organo evaluation | Nourishing effect | A | B | B | B | B | B |
|  | Watery light sensation | B | B | C | C | C | B |
|  | Stickiness free | B | B | B | B | B | B |
|  | Feeling of penetration into skin | A | B | B | B | B | B |
| Outer appearance | Presence of any discoloration | A | A | A | A | A | A |
|  | Stability evaluation | B | C | D | D | D | C |

Examples 10 to 12 and Comparative Example 6

Oil-in-water emulsified cosmetics with different charge neutralizers and contents as listed in Table 2, for Examples 10 to 12 and Comparative Example 6, were prepared by the same method as Examples 1 to 9 and Comparative Examples 1 to 5. The contents (mass %) of each of the materials were as shown in Table 2.

The oil-in-water emulsified cosmetics of Examples 10 to 12 and Comparative Example 6 were supplied for organoleptic evaluation, outer appearance evaluation and long-term stability evaluation by the same methods as Examples 1 to 9 and Comparative Examples 1 to 5. The results are shown in Table 2.

TABLE 2

| | | Ex. 10 | Ex. 11 | Ex. 12 | Comp. Ex. 6 |
|---|---|---|---|---|---|
| A (Aqueous medium) | Butylene glycol | 5 | 5 | 5 | 5 |
| | Pentylene glycol | 2 | 2 | 2 | 2 |
| | Glycerin | 5 | 5 | 5 | 5 |
| | Phenoxyethanol | 0.5 | 0.5 | 0.5 | 0.5 |
| | Water | rem | rem | rem | rem |
| B (Anionic surfactant) | Sodium stearoylglutamate (AMISOFT HS-11 PF) | 1.5 | 1.5 | 1.5 | 1.5 |
| C (Liquid Oil agent) | Dimethylpolysiloxane | 10 | 10 | 10 | 10 |
| | Decamethylcyclopentasiloxane | 10 | 10 | 10 | 10 |
| | Squalane | 5 | 5 | 5 | 5 |
| | Isododecane | 10 | 10 | 10 | 10 |
| | Polyglyceryl-2 triisostearate | 5 | 5 | 5 | 5 |
| | Perfume | 0.1 | 0.1 | 0.1 | 0.1 |
| D (Polymer) | (PEG-240/decyltetradeceth-20/HDI) copolymer (ADEKANOL GT-700) | 0.1 | 0.1 | 0.1 | 0.1 |
| E (Charge neutralizer) | Citric acid | 0.01 | — | — | — |
| | Sodium phosphate | — | 0.01 | — | — |
| | Disodium phosphate | — | 0.06 | — | — |
| | Sodium hydrogensulfite | — | — | 0.01 | — |
| | Total amount (mass %) | 100 | 100 | 100 | 100 |
| Organo evaluation | Nourishing effect | A | A | A | B |
| | Watery light sensation | A | A | A | B |
| | Stickiness free | A | A | A | B |
| | Feeling of penetration into skin | A | A | A | C |
| Outer appearance | Presence of any discoloration | A | A | A | D |
| | Stability Evaluation | A | A | A | B |

Examples 13 to 16 and Comparative Example 7

Oil-in-water emulsified cosmetics with different oil agents, nonionic surfactants and contents as listed in Table 3, for Examples 13 to 16 and Comparative Example 7, were prepared by the same method as Examples 1 to 9 and Comparative Examples 1 to 5. The contents (mass %) of each of the materials were as shown in Table 3.

The oil-in-water emulsified cosmetics of Examples 13 to 16 and Comparative Example 7 were supplied for organoleptic evaluation, outer appearance evaluation and long-term stability evaluation by the same methods as Examples 1 to 9 and Comparative Examples 1 to 5. The results are shown in Table 3.

TABLE 3

| | | Ex. 13 | Ex. 14 | Ex. 15 | Ex. 16 | Comp. Ex. 7 |
|---|---|---|---|---|---|---|
| A (Aqueous medium) | Butylene glycol | 5 | 5 | 5 | 5 | 5 |
| | Pentylene glycol | 2 | 2 | 2 | 2 | 2 |
| | Glycerin | 5 | 5 | 5 | 5 | 5 |
| | Phenoxyethanol | 0.5 | 0.5 | 0.5 | 0.5 | 0.5 |
| | Water | rem | rem | rem | rem | rem |
| B (Anionic surfactant) | Sodium stearoylglutamate (AMISOFT HS-11 PF) | 1.5 | 1.5 | 1.5 | 1.5 | 1.5 |
| C (Liquid Oil agent) | Dimethylpolysiloxane | 12.5 | 10 | 7.5 | 5 | — |
| | Decamethylcyclopentasiloxane | 12.5 | 10 | 7.5 | 5 | — |
| | Squalane | 6.25 | 5 | 3.75 | 2.5 | — |
| | Isododecane | 12.5 | 10 | 7.5 | 5 | — |
| | Polyglyceryl-2 triisostearate | 6.25 | 5 | 3.75 | 2.5 | — |
| | Perfume | 0.1 | 0.1 | 0.1 | 0.1 | 0.1 |
| D (Polymer) | (PEG-240/decyltetradeceth-20/HDI) copolymer (ADEKANOL GT-700) | 0.1 | 0.1 | 0.1 | 0.1 | 0.1 |
| E (Charge neutralizer) | Citric acid | 0.01 | 0.01 | 0.01 | 0.01 | 0.01 |
| | Total amount (mass %) | 100 | 100 | 100 | 100 | 100 |
| Organo evaluation | Nourishing effect | A | A | B | B | D |
| | Watery light sensation | B | A | A | B | D |
| | Stickiness free | A | A | A | B | C |
| | Feeling of penetration into skin | B | A | A | B | C |
| Outer appearance | Presence of any discoloration | A | A | A | A | A |
| | Stability evaluation | A | A | B | B | D |

Example 17 and Comparative Example 8

An oil-in-water emulsified cosmetic with the composition listed in Table 4, for Example 17, was prepared by the same method as Examples 1 to 9 and Comparative Examples 1 to 5. An oil-in-water emulsified cosmetic for Comparative Example 8 was also obtained without high-pressure emulsification with a high-pressure homogenizer, and only stirring with a stirrer at 2500 rpm for 10 minutes. The contents (mass %) of each of the materials were as shown in Table 4.

The oil-in-water emulsified cosmetics of Example 17 and Comparative Example 8 were supplied for organoleptic evaluation, outer appearance evaluation and long-term stability evaluation by the same methods as Examples 1 to 9 and Comparative Examples 1 to 5. The results are shown in Table 4.

TABLE 4

|   |   | Ex. 17 | Comp. Ex.8 |
|---|---|---|---|
| A (Aqueous medium) | Butylene glycol | 5 | 5 |
|  | Pentylene glycol | 2 | 2 |
|  | Glycerin | 5 | 5 |
|  | Phenoxyethanol | 0.5 | 0.5 |
|  | Water | rem | rem |
| B (Anionic surfactant) | Sodium stearoylglutamate (AMISOFT HS-11 PF) | 1.5 | 1.5 |
| C (Polymer) | (PEG-240/decyltetradeceth-20/HDI) copolymer (ADEKANOL GT-700) | 0.1 | 0.1 |
| D (Oil agent) | Dimethylpolysiloxane | 10 | 10 |
|  | Decamethylcyclopentasiloxane | 10 | 10 |
|  | Squalane | 5 | 5 |
|  | Isododecane | 10 | 10 |
|  | Polyglyceryl-2 triisostearate | 5 | 5 |
|  | Perfume | 0.1 | 0.1 |
| E (Charge neutralizer) | Citric acid | 0.01 | 0.01 |
|  | Total amount (mass %) | 100 | 100 |
|  | High-pressure emulsification (200 Mpa) | + | − |
| Organo evaluation | Nourishing effect | A | D |
|  | Watery light sensation | A | D |
|  | Stickiness free | A | C |
|  | Feeling of penetration into skin | A | D |
| Outer appearance | Presence of any discoloration | A | A |
|  | Stability evaluation | A | D |

The invention claimed is:

1. An oil-in-water emulsified cosmetic comprising:
   an aqueous medium;
   an anionic surfactant;
   an oil agent;
   an amphiphilic polymer, selected from the group consisting of hydrophobic group-modified hydrophilic urethane polymers, (meth)acrylic polymers having a side chain including a hydrophilic group and a hydrophobic group, and hydrophobic group-modified hydrophilic polysaccharides; and
   a charge neutralizer,
   wherein the cosmetic has a viscosity of 10,000 mPa·s or higher at 25° C.

2. The oil-in-water emulsified cosmetic according to claim 1, wherein the oil agent content ratio is 20 mass % or greater based on the total mass of the oil-in-water emulsified cosmetic.

3. The oil-in-water emulsified cosmetic according to claim 1, wherein the hydrophobic group-modified hydrophilic urethane polymer is present and contains a hydrophobic group-modified polyether-urethane including polyalkylene oxide component.

4. The oil-in-water emulsified cosmetic according to claim 1, wherein the hydrophobic group-modified hydrophilic polysaccharide is present and contains a hydrophobic group-modified hydroxyalkyl alkylcellulose.

5. The oil-in-water emulsified cosmetic according to claim 1, wherein the oil agent comprises a non-polar oil, a silicone oil or a mixture thereof.

6. The oil-in-water emulsified cosmetic according to claim 1, wherein the oil-in-water emulsified cosmetic is obtainable by high-pressure emulsification at a pressure of 100 MPa or greater.

7. A process for preparing the oil-in-water emulsified cosmetic according to claim 1 comprising a step of emulsifying a mixture of components (A) to (E) in a high-pressure homogenizer at a pressure of 100 MPa or higher.

8. A method of skin nourishing comprising a step of applying on skin an oil-in-water emulsified cosmetic according to claim 1.

9. The oil-in-water emulsified cosmetic according to claim 3, wherein the hydrophobic group-modified hydrophilic urethane polymer contains polyethylene oxide and/or polypropylene oxide.

* * * * *